(12) United States Patent
Tokunaga et al.

(10) Patent No.: US 9,487,475 B2
(45) Date of Patent: Nov. 8, 2016

(54) PREPARATION METHOD OF ALDEHYDE COMPOUND WITH LIMITED AMOUNT OF ACRYLONITRILE

(71) Applicant: MITSUI CHEMICALS, INC., Minato-ku, Tokyo (JP)

(72) Inventors: Koichi Tokunaga, Chikugo (JP); Naoyuki Kakinuma, Omuta (JP); Shigetoshi Kuma, Kurume (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/440,992

(22) PCT Filed: Nov. 8, 2013

(86) PCT No.: PCT/JP2013/080317
§ 371 (c)(1),
(2) Date: May 6, 2015

(87) PCT Pub. No.: WO2014/073664
PCT Pub. Date: May 15, 2014

(65) Prior Publication Data
US 2015/0299109 A1  Oct. 22, 2015

(30) Foreign Application Priority Data

Nov. 9, 2012  (JP) .................................. 2012-247510

(51) Int. Cl.
*C07C 255/47* (2006.01)
*C07C 211/38* (2006.01)
(Continued)

(52) U.S. Cl.
CPC .............. *C07C 255/47* (2013.01); *B01J 31/24* (2013.01); *C07C 211/19* (2013.01); *C07C 211/38* (2013.01); *C07C 265/14* (2013.01); *C07C 2102/40* (2013.01); *C07C 2102/42* (2013.01)

(58) Field of Classification Search
CPC .............. C07C 2102/42; C07C 211/19; C07C 211/38; C07C 255/47; C07C 255/46
See application file for complete search history.

(56) References Cited

U.S. PATENT DOCUMENTS

| 3,143,570 A | 8/1964 | Caldwell et al. |
| 4,642,395 A | 2/1987 | Hunter et al. |

(Continued)

FOREIGN PATENT DOCUMENTS

| EP | 0065294 A1 | 11/1982 |
| EP | 2708527 A1 | 3/2014 |

(Continued)

OTHER PUBLICATIONS

Yanagi, Yoshio—JP 60-072844—translation—PD: Apr. 24, 1985.*

(Continued)

*Primary Examiner* — Valerie Rodriguez-Garcia
(74) *Attorney, Agent, or Firm* — Buchanan, Ingersoll & Rooney PC

(57) ABSTRACT

A preparation method of an aldehyde compound of the present invention includes a step of reacting a compound represented by the following general formula (a1) with hydrogen and carbon monoxide in the presence of a metal compound including 0.01 ppmmol to 10 ppmmol of a metal belonging to Groups 8 to 10 with respect to 1 mole of the compound and a phosphorus compound, and in the step, the amount of acrylonitrile included in the compound represented by the general formula (a1) is equal to or less than 200-fold by mole with respect to 1 mole of the metal belonging to Groups 8 to 10.

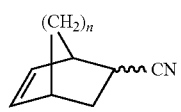

(a1)

5 Claims, 3 Drawing Sheets

(51) Int. Cl.
*C07C 211/19* (2006.01)
*B01J 31/24* (2006.01)
*C07C 265/14* (2006.01)

(56) References Cited

U.S. PATENT DOCUMENTS

| | | | |
|---|---|---|---|
| 4,960,949 | A | 10/1990 | Devon et al. |
| 5,004,823 | A | 4/1991 | Devon et al. |
| 5,312,996 | A | 5/1994 | Packett |
| 2010/0324339 | A1 | 12/2010 | Choi et al. |

FOREIGN PATENT DOCUMENTS

| | | | |
|---|---|---|---|
| GB | 1402832 | A | 8/1975 |
| JP | 60-072844 | A | 4/1985 |
| JP | 64-040434 | * | 2/1989 |
| JP | 64-40434 | A | 2/1989 |
| JP | 04-502463 | A | 5/1992 |
| JP | 06-184036 | A | 7/1994 |
| JP | 7-17909 | A | 1/1995 |
| JP | 2001-261660 | A | 9/2001 |
| JP | 2002-348271 | A | 12/2002 |
| JP | 2003-505438 | A | 2/2003 |
| JP | 2008-031125 | A | 2/2008 |
| JP | 2010-538816 | A | 12/2010 |
| WO | WO 90/06810 | A1 | 6/1990 |
| WO | WO 93/03839 | A1 | 3/1993 |
| WO | WO 01/07382 | A2 * | 2/2001 |
| WO | WO 2009/035204 | A1 | 3/2009 |
| WO | WO 2012/153509 | A1 | 11/2012 |

OTHER PUBLICATIONS

Fukada—JP 2002/348271 raw machine translation—: PD: Dec. 4, 2002.*
International Search Report (PCT/ISA/210) mailed on Feb. 4, 2014, by the Japanese Patent Office as the International Searching Authority for International Application No. PCT/JP2013/080344.
International Search Report (PCT/ISA/210) mailed on Feb. 4, 2014, by the Japanese Patent Office as the International Searching Authority for International Application No. PCT/JP2013/080317.
Fermann et al.: "Umlagerungen von 5- und 6-Cyan-2-norbornyl-Kationen," Chemische Berichte, vol. 122, No. 5, May 1, 1989, pp. 975-984.
Extended Search Report issued by the European Patent Office in corresponding European Patent Application No. 13854059.6 on May 9, 2016 (8 pages).
Extended Search Report issued by the European Patent Office in related European Patent Application No. 13853896.2 on Jun. 13, 2016 (9 pages).

* cited by examiner

PREPARATION METHOD OF ALDEHYDE COMPOUND WITH LIMITED AMOUNT OF ACRYLONITRILE

TECHNICAL FIELD

The present invention relates to a preparation method of an aldehyde compound, a preparation method of an amine compound and a preparation method of an isocyanate compound using the aldehyde compound obtained by the preparation method.

BACKGROUND ART

As a preparation method of an aldehyde compound using norbornene compound, for example, methods described in Patent Documents 1 to 3 are known.

Patent Documents 1 to 3 disclose methods for preparing formyl cyan norbornene by hydroformylating cyan norbornene using a mixed $H_2$/CO gas in the presence of a catalyst. Patent Documents 1 and 2 disclose an example using a metal compound as a catalyst. Moreover, since it is possible to obtain a target compound with high selectivity, and it is possible to suppress the reaction pressure to be low, a rhodium complex is preferably used as the catalyst.

Patent Document 1 describes that the catalyst may be used at 0.1% by weight to 10% by weight with respect to cyan norbornene. Patent Document 2 describes that with the catalyst concentration of 0.5 mmol/l to 10 mmol/l, triarylphosphine can be used in a range of 3 moles to 300 moles with respect to 1 mole of rhodium.

Patent Document 4 discloses a method of hydroformylating an olefin-based compound using a mixed $H_2$/CO gas in the presence of a transition metal catalyst and a trivalent phosphorus compound. Furthermore, it is described that as the content of the metal catalyst, a free metal content is 10 ppm to 1,000 ppm based on the weight or volume of the catalyst composition.

Patent Document 5 describes a metal ligand complex catalyst, and exemplifies rhodium as a metal and an organic phosphorus ligand as a ligand. In addition, it is described that the amount of these used, in a case of calculating as a free metal, is a metal concentration in a range of about 1 ppm to 10,000 ppm, and a molar ratio of ligand:metal is 1:1 to 200:1.

In addition, Patent Document 6 discloses a method of preparing an aldehyde compound by hydroformylating a linear olefin compound.

In Examples of Patent Document 6, an example of hydroformylating 7-octenal in the presence of a rhodium catalyst and bisphosphite is described. In addition, it is described that about 3 ppmmol of rhodium is used with respect to 1 mole of 7-octenal, and rhodium atoms/phosphorus atoms is 1/20 as a molar ratio. On the other hand, in paragraph 0084 of Patent Document 6, it is described that 2 moles to 1,000 moles in terms of phosphorus atom is preferable with respect to 1 mole of a metal, and in a case of exceeding 1,000 moles, the reaction rate tends to be extremely low.

RELATED DOCUMENT

Patent Document

[Patent Document 1] Japanese Laid-open Patent Publication No. 57-193438
[Patent Document 2] Japanese Laid-open Patent Publication No. 60-72844
[Patent Document 3] U.S. Pat. No. 3,143,570
[Patent Document 4] Japanese Translation of PCT International Application No. 2010-538818
[Patent Document 5] Japanese Translation of PCT International Application No. 2003-505438
[Patent Document 6] Japanese Laid-open Patent Publication No. 2008-031125

DISCLOSURE OF THE INVENTION

In recent years, the amount of rare metal used has increased with technological developments, and depletion of rare metal resources and rising prices have become a problem. Therefore, reducing the amount of so-called rare metals used and effective use thereof have been widely sought.

However, it is found that in the hydroformylation reaction of a norbornene compound, for example, cyanonorbornene, when reducing the amount of a metal compound which is a catalyst, a problem in productivity such as decrease in the reaction rate or decrease in the yield due to stopping of the reaction itself occurs. In industrial production, decrease in the reaction rate causes a problem in connection to the next step, and thus, production cannot be efficiently performed.

The present invention has been made in consideration of the above problems, and an object of the present invention is to provide an industrially advantageous method in which the amount of a metal which is an expensive catalyst is reduced, and which can suppress decrease in the reaction rate even in a case where the amount of the metal is reduced when aldehyde is prepared.

As a result of thorough studies of factors decreasing the reaction rate in order to solve the above problems, the present inventor found that when acrylonitrile is present in the reaction system, the reaction rate is decreased. Furthermore, the present inventor found that by controlling the amount of the acrylonitrile, it is possible to prepare aldehyde without a decrease in the reaction rate, and made the present invention.

The present invention can be described as follows.

[1] A preparation method of an aldehyde compound having a step of reacting a compound represented by the following general formula (a1) with hydrogen and carbon monoxide in the presence of a metal compound including 0.01 ppmmol to 10 ppmmol of a metal belonging to Groups 8 to 10 with respect to 1 mole of the compound and a phosphorus compound, in which the amount of acrylonitrile included in the compound represented by the general formula (a1) in the step is equal to or less than 200-fold by mole with respect to 1 mole of the metal belonging to Groups 8 to 10.

(a1)

(In the formula (a1), n represents 0, 1, or 2.)

[2] The preparation method of an aldehyde compound according to [1], in which the metal compound including the metal belonging to Groups 8 to 10 is a rhodium compound, a cobalt compound, a ruthenium compound, or an iron compound.

[3] The preparation method of an aldehyde compound according to [1] or [2], in which the metal compound including the metal belonging to Groups 8 to 10 is a rhodium compound.

[4] The preparation method of an aldehyde compound according to any one of [1] to [3], in which the amount of the metal belonging to Groups 8 to 10 is 1 ppmmol to 5 ppmmol with respect to 1 mole of the compound represented by the general formula (a1).

[5] The preparation method of an aldehyde compound according to any one of [1] to [4], in which the phosphorus compound is a trivalent phosphorus compound.

[6] The preparation method of an aldehyde compound according to any one of [1] to [5], in which the compound represented by the general formula (a1) is a compound represented by the following chemical formula (1).

(1)

[7] A preparation method of an amine compound, including a step of reacting the aldehyde compound obtained by the preparation method according to any one of [1] to [6] with ammonia, and with hydrogen in the presence of a catalyst.

[8] A preparation method of an isocyanate compound including a step of reacting the amine compound obtained by the preparation method according to [7] with a carbonylating agent.

Moreover, the "phosphorous compound" in the present invention means a phosphorous compound capable of forming a complex with a metal belonging to Groups 8 to 10.

In addition, in the present invention, in a case where a material B is used in the amount of $1\times10^{-6}$ moles with respect to 1 mole of a material A, the amount of the material B is indicated as 1 ppmmol.

According to the preparation method of an aldehyde compound of the present invention, a decrease in the reaction rate generated when the amount of metal which is a catalyst is reduced is suppressed, and industrially advantageous preparation of an aldehyde compound can be achieved. Since the preparation method of an amine compound and the preparation method of an isocyanate compound of the present invention include the preparation method of an aldehyde compound as one step, according to the present invention, the effect is exhibited that productivity and yield of the isocyanate compound and the amine compound also are excellent.

BRIEF DESCRIPTION OF THE DRAWINGS

The above-described objects, other objects, features, and advantages will be made clearer from the preferred embodiments described below, and the following accompanying drawings.

DESCRIPTION OF EMBODIMENTS

Hereinafter, the preparation method of an aldehyde compound of the present embodiment will be described, and the preparation method of an amine compound, and then, the preparation method of an isocyanate compound will be described.

The compound represented by the following general formula (a1) (hereinafter, referred to as the compound (a1)) used in the preparation method of an aldehyde compound of the present embodiment is synthesized through a Diels-Alder reaction of acrylonitrile and a compound having a conjugated double bond.

(a1)

In the formula (a1), n represents 0, 1, or 2, and 0 or 1 is preferable, and 1 is more preferable.

Moreover, the compound (a1) may be an endo compound or an exo compound, and may be a mixture including these in arbitrary proportions.

Examples of the compound having a conjugated double bond include butadiene, cyclopentadiene, and 1,3-cyclohexadiene. Moreover, since cyclopentadiene which is a raw material is present as dicyclopentadiene which is a dimer under the conditions of room temperature and atmospheric pressure, and the dicyclopentadiene is decomposed under the reaction conditions, producing cyclopentadiene, in general, dicyclopentadiene is used in the reaction. In the present embodiment, dicyclopentadiene is preferably used.

This step can be performed under the conditions of a reaction temperature of 100° C. to 250° C. and a reaction time of 0.1 hours to 10 hours. Acrylonitrile included in the compound (a1) is an unreacted material in the preparation step. Specifically, an unreacted acrylonitrile is included in the reaction liquid obtained after synthesizing the compound (a1).

In the step, the amount of acrylonitrile is adjusted such that the amount of acrylonitrile in the synthesis step of an aldehyde compound described below becomes equal to or less than 200-fold by mole, preferably equal to or less than 140-fold by mole, and more preferably equal to or less than 50-fold by mole with respect to 1 mole of the metal belonging to Groups 8 to 10. Although the lower limit value is not particularly limited, the lower limit value is preferably equal to or greater than 0.05-fold by mole. When the lower limit value is the above value, the step of reducing the amount of acrylonitrile is simple and does not influence productivity, and thus, it is preferable. Moreover, the upper limit value and the lower limit value can be suitably combined.

Specifically, a method of adjusting the above reaction conditions or the amount of acrylonitrile as a raw material such that the amount of acrylonitrile included in the reaction liquid after synthesizing the compound (a1) becomes the above amount, or a method of adjusting the amount of acrylonitrile to the above amount by reducing the amount of acrylonitrile included in the reaction liquid after synthesizing the compound (a1) can be exemplified. As the method of reducing the amount of acrylonitrile, distillation under decreased pressure, purification using a column, or the like can be exemplified, however, the method is not particularly limited.

<Preparation Method of Aldehyde Compound>

The compound (a1) including acrylonitrile in a predetermined range is allowed to react with hydrogen and carbon monoxide in the presence of "a metal compound including a metal belonging to Groups 8 to 10" in 0.01 ppmmol to 10 ppmmol with respect to 1 mole of the compound (a1) and a phosphorus compound. Specifically, the above reaction can be performed on the compound (a1) in which the amount of acrylonitrile is adjusted, in a state in which the amount of acrylonitrile in the reaction system is adjusted to the amount in the above range.

In the present embodiment, n of the compound (a1) is more preferably 1. Specifically, the compound is represented by the following chemical formula (1).

(1)

Moreover, the compound represented by the chemical formula (1) may be an endo compound or an exo compound, and may be a mixture including these in arbitrary proportions.

The metal compound including a metal belonging to Groups 8 to 10 used in the reaction of the present embodiment is a rhodium compound, a cobalt compound, a ruthenium compound, or an iron compound.

Examples of the rhodium compound include $Rh(acac)(CO)_2$, $Rh(acac)_3$, $RhCl(CO)(PPh_3)_2$, $RhCl(PPh_3)_3$, $RhBr(CO)(PPh_3)_2$, $Rh_2(CO)_8$, $Rh_4(CO)_{12}$, and $Rh_6(CO)_{16}$. Examples of the cobalt compound include $HCo(CO)_3$, $HCo(CO)_4$, $Co_2(CO)_8$, and $HCo_3(CO)_9$. Examples of the ruthenium compound include $Ru(CO)_3(PPh_3)_2$, $RuCl_2(PPh_3)_3$, $RuCl_3(PPh_3)_3$, and $Ru_3(CO)_{12}$. In addition, examples of the iron compound include $Fe(CO)_5$, $Fe(CO)_4PPh_3$, and $Fe(CO)_4(PPh_3)_2$. Moreover, "acac" means acetylacetonato.

The rhodium compound used in the reaction of the present embodiment is not particularly limited as long as it is a compound including monovalent rhodium metal, and rhodium carbonyl catalysts such as dicarbonylacetylacetonato rhodium ($Rh(acac)(CO)_2$) dodecacarbonyl tetrarhodium ($Rh_4(CO)_{12}$), hexadecacarbonyl hexarhodium ($Rh_6(CO)_{16}$), and octacarbonyl dirhodium ($Rh_2(CO)_8$); and rhodium chloride can be exemplified.

The phosphorus compound used in the reaction of the present embodiment is not particularly limited as long as it is a trivalent phosphorus compound, and the compound represented by the following formula is preferably used.

$(R^1)_3P$ $(R^2O)_3P$

In the above formula, $R^1$ and $R^2$ may be the same as or different from each other, and each of $R^1$ and $R^2$ represents an alkyl group having 1 to 16 carbon atoms or an aryl group having 6 to 16 carbon atoms which may have a substituent.

As the phosphorus compound, specifically, trivalent phosphorus compounds such as triphenyl phosphite, triphenyl phosphine, trimethyl phosphine, triethyl phosphine, tripropyl phosphine, tri(methyl benzene)phosphine, tri(ethyl benzene)phosphine, 1,2-bis(diphenyl phosphino)ethylene, 1,3-bis(diphenyl phosphino)propane, 2,2-bis(diphenyl phosphino)-1,1-binaphthyl, trimethoxy phosphite, triethoxy phosphite, tripropoxy phosphite, triisopropoxy phosphite, trimethylphenyl phosphite, and tris(2,4-di-tert-butylphenyl) phosphite can be exemplified.

In the hydroformylation reaction using these raw materials, the amount of metal belonging to Groups 8 to 10 to be used is 0.01 ppmmol to 10 ppmmol, and preferably 1 ppmmol to 10 ppmmol, and more preferably 1 ppmmol to 5 ppmmol with respect to 1 mole of the compound (a1). When the amount is in the above numerical range, it is possible to ensure smooth progress of the reaction without excessively using an expensive catalyst.

In addition, the amount of phosphorus compound used is preferably equal to or greater than 100-fold by mole, and more preferably equal to or greater than 100-fold by mole and equal to or less than 10,000-fold by mole with respect to the metal belonging to Groups 8 to 10.

Moreover, the above numerical range can be combined arbitrarily.

Synthesis of the aldehyde compound, specifically, can be performed in the following manner.

First, a rhodium compound, a phosphorus compound, and a compound (a1) which is a raw material are put in a reactor. While supplying ng hydrogen and a carbon monoxide gas thereto, the mixture is allowed to react at a temperature of 30° C. to 120° C. and a pressure of 0.1 MPa to 1.0 MPa for 1 hour to 8 hours. Moreover, the hydroformylation reaction can be performed by suitably selecting a homogeneous reaction system configured of only an oil phase or a two-layer reaction system configured of a water layer and an oil layer.

Thus, the compound (a1) is hydroformylated, whereby an aldehyde compound is synthesized.

Moreover, the hydroformylation reaction can also be performed without a solvent, or can be performed using a substituted or unsubstituted aromatic compound, a substituted or unsubstituted aliphatic hydrocarbon compound, or alcohol, and for example, the hydroformylation reaction can also be performed in a solvent such as toluene, benzene, hexane, octane, acetonitrile, benzonitrile, ortho-dichlorobenzene, ethanol, pentanol, or octanol. The hydroformylation reaction in the present embodiment is also excellent in reactivity at a high concentration, and thus, the hydroformylation reaction can be performed without a solvent. As a result, since a step of distilling off a solvent or the like is not required, the step becomes simple, the volume efficiency also is improved, and the production efficiency also is excellent.

The aldehyde compound represented by the following general formula (b1) is synthesized from the compound of the general formula (a1) by the preparation method of the present embodiment.

(b1)

In a case where n is 1 or 2, the compound represented by the general formula (b1) can be obtained as any one of "a compound in which the 2-position and the 5-position are substituted with predetermined groups (hereinafter, referred to as a 2,5-isomer)" and "a compound in which the 2-position and the 6-position are substituted with predetermined groups (hereinafter, referred to as a 2,6-isomer)", or can be obtained as a mixture including these in arbitrary proportions. In addition, each of the 2,5-isomer and the 2,6-isomer can be obtained as any one of an endo-endo compound, an endo-exo compound, and an exo-exo compound depending on a steric configuration of the substituent, or can be obtained as a mixture including at least two types of these in arbitrary proportions.

Moreover, in a case where n is 0, the compound represented by the general formula (b1) can be obtained as any one of a cis-type and a trans-type, or can also be obtained as a mixture including these in arbitrary proportions.

In the general formula (b1), n is the same as that in the general formula (a1).

In the present embodiment, the compound represented by the general formula (b1) is preferably obtained, and as the compound, the compound represented by the following chemical formula (2) can be exemplified.

(2)

Moreover, the aldehyde compound represented by the chemical formula (2) can be obtained as any one of "a compound in which the 2-position of bicyclo[2.2.1]heptane is substituted with a cyano group and the 5-position is substituted with an aldehyde group (hereinafter, referred to as a 2,5-isomer)" and "a compound in which the 2-position is substituted with a cyano group and the 6-position is substituted with an aldehyde group (hereinafter, referred to as a 2,6-isomer)", or can be obtained as a mixture including these in arbitrary proportions. In addition, each of the 2,5-isomer and the 2,6-isomer can be obtained as any one of an endo-endo compound, an endo-exo compound, and an exo-exo compound depending on a steric configuration of the substituent, or can be obtained as a mixture including at least two types of these in arbitrary proportions.

After the hydroformylation reaction is finished, a target aldehyde compound can be obtained by performing a predetermined purification step.

<Preparation Method of Amine Compound>

The preparation method of an amine compound of the present embodiment includes the following steps.

Step (a): Using the compound (a1) including acrylonitrile in a predetermined range, the compound (a1) is allowed to react with hydrogen and carbon monoxide in the presence of a metal compound including a metal belonging to Groups 8 to 10 and a phosphorus compound.

Step (b): The aldehyde compound obtained in the step (a) is reacted with ammonia, and reacted with hydrogen in the presence of a catalyst.

The preparation method of an amine compound of the present embodiment includes the preparation method of an aldehyde compound described above as the step (a). Therefore, in the step (a), the aldehyde compound can be industrially advantageously prepared by the method in the present invention, and thus, improvement in the productivity and yield of the amine compound which is a target compound becomes excellent.

Moreover, since the step (a) is the same as the step in the above-described "the preparation method of an aldehyde compound", the description thereof will not be repeated.

In the step (b), by performing imination by reacting the aldehyde compound obtained in the step (a) and represented by the general formula (b1) with ammonia and hydrogenation in the presence of a catalyst, an amine compound is synthesized.

As the catalyst, metal catalysts such as nickel, platinum, palladium, and ruthenium can be used. In a case where the aldehyde compound has a cyano group as a substituent, a —CH$_2$—NH$_2$ group is produced by hydrogen reduction.

In this manner, in the step (b), the aldehyde group of the aldehyde compound becomes an amino group by imination, and the cyano group also becomes an amino group by hydrogen reduction, and thus, the amine compound represented by the following general formula (c1) having two amino groups is synthesized.

(c1)

In the formula (c1), n is the same as that in the general formula (a1).

In a case where n is 1 or 2, the compound represented by the general formula (c1) can be obtained as any one of "a compound in which the 2-position and the 5-position are substituted with predetermined groups (hereinafter, referred to as a 2,5-isomer)" and "a compound in which the 2-position and the 6-position are substituted with predetermined groups (hereinafter, referred to as a 2,6-isomer)", or can be obtained as a mixture including these in arbitrary proportions. In addition, each of the 2,5-isomer and the 2,6-isomer can be obtained as any one of an endo-endo compound, an endo-exo compound, and an exo-exo compound depending on a steric configuration of the substituent, or can be obtained as a mixture including at least two types of these in arbitrary proportions.

Moreover, in a case where n is 0, the compound represented by the general formula (c1) can be obtained as any one of a cis-type and a trans type, or can also be obtained as a mixture including these at an arbitrary proportion.

The compound of the general formula (c1) is preferably obtained, and as the compound, the compound represented by the following chemical formula (3) in which n is 1 can be exemplified.

(3)

Moreover, the amine compound represented by the chemical formula (3) can be obtained as any one of "a compound in which the 2-position and the 5-position of bicyclo[2.2.1]heptane are substituted with aminomethyl groups (hereinafter, referred to as a 2,5-isomer)" and "a compound in which the 2-position and the 6-position are substituted with aminomethyl groups (hereinafter, referred to as a 2,6-isomer)", or can be obtained as a mixture including these in arbitrary proportions. In addition, each of the 2,5-isomer and the 2,6-isomer can be obtained as any one of an endo-endo compound, an endo-exo compound, and an exo-exo compound depending on a steric configuration of the substituent, or can be obtained as a mixture including at least two types of these in arbitrary proportions.

The above imination and hydrogenation reaction, specifically, can be performed in the following manner. First, an aldehyde compound, a solvent, and a catalyst are introduced into a reactor, and an ammonia gas is blown thereinto. Furthermore, hydrogen is injected at a pressure until the pressure in the reactor becomes about 1 MPa, then, the temperature is raised to about 100° C., and the reaction is allowed to proceed for about 1 hour to 10 hours at this temperature and pressure while supplying hydrogen. As the solvent, for example, an alcohol having 1 to 8 carbon atoms or water is preferably used.

Furthermore, after the reaction is finished, general catalyst filtration, desolventizing, and a purification step are performed, whereby a target amine compound can be obtained.

<Preparation Method of Isocyanate Compound>

The preparation method of an isocyanate compound of the present embodiment includes the following steps.

Step (a): Using the compound (a1) including acrylonitrile in a predetermined range, the compound (a1) is allowed to react with hydrogen and carbon monoxide in the presence of a metal compound including a metal belonging to Groups 8 to 10 and a phosphorus compound.

Step (b): The aldehyde compound obtained in the step (a) is reacted with ammonia, and reacted with hydrogen in the presence of a catalyst.

Step (c): The amine compound obtained in the step (b) is reacted with a carbonylating agent.

The preparation method of an isocyanate compound of the present embodiment includes the preparation method of an aldehyde compound described above as the step (a). Therefore, in the step (a), the aldehyde compound can be industrially advantageously prepared by the method in the present invention, and thus, the productivity and yield of the isocyanate compound which is a target compound also become excellent.

Moreover, since the step (a) is the same as the step in the above-described "the preparation method of an aldehyde compound", and the step (b) is the same as the step in the above-described "the preparation method of an amine compound", the description thereof will not be repeated.

In the step (c), by reacting the amine compound obtained in the step (b) represented by the general formula (c1) with a carbonylating agent under predetermined conditions, an isocyanate compound represented by the following general formula (d1) is synthesized. As the carbonylating agent, phosgene, urea derivatives, carbonate derivatives, or carbon monoxide can be used.

(d1)

In the formula (d1), n is the same as that in the general formula (a1).

In a case where n is 1 or 2, the compound represented by the general formula (d1) can be obtained as any one of "a compound in which the 2-position and the 5-position are substituted with predetermined groups (hereinafter, referred to as a 2,5-isomer)" and "a compound in which the 2-position and the 6-position are substituted with predetermined groups (hereinafter, referred to as a 2,6-isomer)", or can be obtained as a mixture including these in arbitrary proportions. In addition, each of the 2,5-isomer and the 2,6-isomer can be obtained as any one of an endo-endo compound, an endo-exo compound, and an exo-exo compound depending on a steric configuration of the substituent, or can be obtained as a mixture including at least two types of these in arbitrary proportions.

Moreover, in a case where n is 0, the compound represented by the general formula (d1) can be obtained as any one of a cis-type and a trans-type, or can also be obtained as a mixture including these in arbitrary proportions.

The compound of the general formula (d1) is preferably obtained, and as the compound, the compound represented by the following chemical formula (4) in which n is 1 can be exemplified.

(4)

Moreover, the isocyanate compound represented by the chemical formula (4) can be obtained as any one of "a compound in which the 2-position and the 5-position of bicyclo[2.2.1]heptane are substituted with isocyanatomethyl groups (hereinafter, referred to as a 2,5-isomer)" and "a compound in which the 2-position and the 6-position are substituted with isocyanatomethyl groups (hereinafter, referred to as a 2,6-isomer)", or can be obtained as a mixture including these in arbitrary proportions. In addition, each of the 2,5-isomer and the 2,6-isomer can be obtained as any one of an endo-endo compound, an endo-exo compound, and an exo-exo compound depending on a steric configuration of the substituent, or can be obtained as a mixture including at least two types of these in arbitrary proportions.

In a case of using phosgene as a carbonylating agent, as the step (c), specifically, a method in which first, an amine compound and a solvent are introduced into a reactor, then, the mixture is subjected to a hydrochlorination reaction using hydrochloric acid then, and reacted with phosgene or a method in which a carbamoyl chloride compound is obtained by directly reacting with phosgene, and the obtained carbamoyl chloride compound is subjected to a thermal decomposition can be exemplified. Furthermore, after the reaction is finished, a general purification step is performed, whereby a target isocyanate compound can be obtained.

Moreover, although the reaction solvent in a case of using phosgene as a carbonylating agent is not particularly limited, an organic aromatic compound having a high boiling point or an ester compound which has a high solubility of hydrochloric acid at the time of a salt formation reaction and a high solubility of phosgene and a low solubility of hydrochloric acid at the time of a phosgenation reaction are preferably used. Examples of the organic aromatic compound having a high boiling point include 1,2-diethylbenzene, 1,3-diethylbenzene, 1,4-diethylbenzene, isopropylbenzene, 1,2,4-trimethylbenzene, amylbenzene, diamylbenzene, triamylbenzene, dodecylbenzene, p-cymene, cumene methylphenyl ether, ethylphenyl ether, diisoamyl ether, n-hexyl ether, ortho-dichlorobenzene, para-chlorotoluene, bromobenzene, and 1,2,4-trichlorobenzene. In addition, although the ester compound is not particularly limited, acetic esters such as isoamyl acetate and isooctyl acetate are preferable. Among these exemplified solvents, a particularly preferred solvent for performing the present invention is an aromatic halogen compound.

The isocyanate compound obtained by the present embodiment can be used as a raw material of optical materials or paint. Moreover, the amine compound obtained by the present embodiment can be used as paint or a raw material for a curing agent.

EXAMPLES

Hereinafter, the present invention will be further described in more detail with Examples, and the scope of the present invention is not limited to Examples.

Reference Example

Synthesis of bicyclo[2.2.1]-5-heptene-2-carbonitrile 195.0 g (1.40 mol) of dicyclopentadiene having a purity of 95% and 163.6 g (3.08 mol) of acrylonitrile in which 0.36 g (1.8 mmol) of N-nitrosodiphenylamine was added were introduced into a 1,000 mL autoclave, then, the mixture was allowed to react at 160° C. for 5 hours with stirring, and after the temperature was raised to 180° C. and the resultant product was allowed to react for 2 hours, the reaction was finished. 355.6 g of reaction liquid including bicyclo[2.2.1]-5-heptene-2-carbonitrile was obtained, and when analysis of the reaction liquid was performed, 331.2 g (2.78 mol) of bicyclo[2.2.1]-5-heptene-2-carbonitrile was found to be contained therein. 352.4 g of a reaction liquid including 328.2 g (2.75 mol) of the obtained bicyclo[2.2.1]-5-heptene-2-carbonitrile was obtained.

Example 1

Synthesis of 2-cyano-5-formyl bicyclo[2.2.1]heptane and 2-cyano-6-formyl bicyclo[2.2.1]heptane 50.0 mg (0.194 mmol) of rhodium acetylacetonatodicarbonyl and 16.0 g (0.133 mol) of the bicyclo[2.2.1]-5-heptene-2-carbonitrile, and 1.2 g (3.87 mmol) of triphenyl phosphite were introduced into a glass container having an internal volume of 0.1 L, then, the mixture was stirred at 25° C., and a catalyst master liquid was adjusted. Then, 0.81 g (0.009 mmol in terms of Rh) of the catalyst master liquid and 218.6 g (1.8 mol) of bicyclo[2.2.1]-5-heptene-2-carbonitrile obtained as a main fraction by distilling the reaction liquid obtained by the method in Reference Example under decreased pressure, and 5.656 g (18.23 mmol) of triphenyl phosphite were introduced into an electromagnetic stirring type autoclave made of SUS316L having an internal volume of 0.5 L, and the mixture was stirred at 25° C., whereby 225.1 g of a Rh catalyst adjusting liquid was obtained. When the amount of acrylonitrile included in the bicyclo[2.2.1]-5-heptene-2-carbonitrile at this time was measured by the following analytical method, the result was 0.1 ppm (0.0004 mmol). The amount corresponds to 0.05-fold by mole with respect to 1 mole of rhodium.

Amount of rhodium used: 5 ppmmol with respect to 1 mole of bicyclo[2.2.1]-5-heptene-2-carbonitrile

[Quantitative Analysis Method of Acrylonitrile]

GC model: GC-2014, manufactured by Shimadzu Corporation

Column: DB-5, manufactured by J&W Scientific, inner diameter of 0.53 mm, length of 60 m, and thickness of 1.5 μm Temperature conditions: Column of 60° C., inlet of 150° C., detector of 300° C.

Carrier gas: Nitrogen

Injection volume: 1 μL

Then, after sufficiently replacing with nitrogen, replacement by a mixed gas having a volume ratio of carbon monoxide/hydrogen of 50/50 was sufficiently performed. The same gas was supplied until the pressure in the autoclave became 0.6 MPaG, and under stirring, the temperature was raised to 80° C., whereby a hydroformylation reaction was started. Since the pressure in the autoclave was decreased with the progress of the reaction, the mixed gas was continuously supplied such that the pressure was maintained at 0.6 MPaG, the liquid temperature was adjusted so as to be maintained at 80° C., and a reaction was performed for 4.5 hours. After the reaction was finished, the mixed gas in the system was purged with nitrogen, whereby 275.0 g of a reaction liquid including 2-cyano-5(6)-formyl bicyclo[2.2.1]heptane was obtained. When analysis of the reaction liquid was performed, 259.4 g (1.74 mol) of 2-cyano-5-formyl bicyclo[2.2.1]heptane and 2-cyano-6-formyl bicyclo[2.2.1]heptane was found to be contained therein. The reaction yield was 96.7 mol %. The results are shown in Table 1.

255.1 g (1.71 mol) of 2-cyano-5(6)-formyl bicyclo[2.2.1]heptane, 263.8 g of a reaction liquid including 4.7 g (0.02 mol) of triphenyl phosphite, and 14.0 g of water were introduced into a four-neck reaction flask having an internal volume of 2 L equipped with a reflux condenser, a stirring blade, and a thermometer, and after stirring the mixture, the temperature was raised to 80° C., and hydrolysis was performed for 2 hours. When analysis of the obtained solution was performed, 252.1 g (1.69 mol) of 2-cyano-5-formyl bicyclo[2.2.1]heptane and 2-cyano-6-formyl bicyclo[2.2.1]heptane was found to be contained therein, and triphenyl phosphite was not detected.

6.4 g (0.012 mol) of 20% by weight aqueous potassium hydrogencarbonate solution of was added dropwise to the hydrolyzed solution so as to give pH of 7.0 at 25° C.

Figure 1:
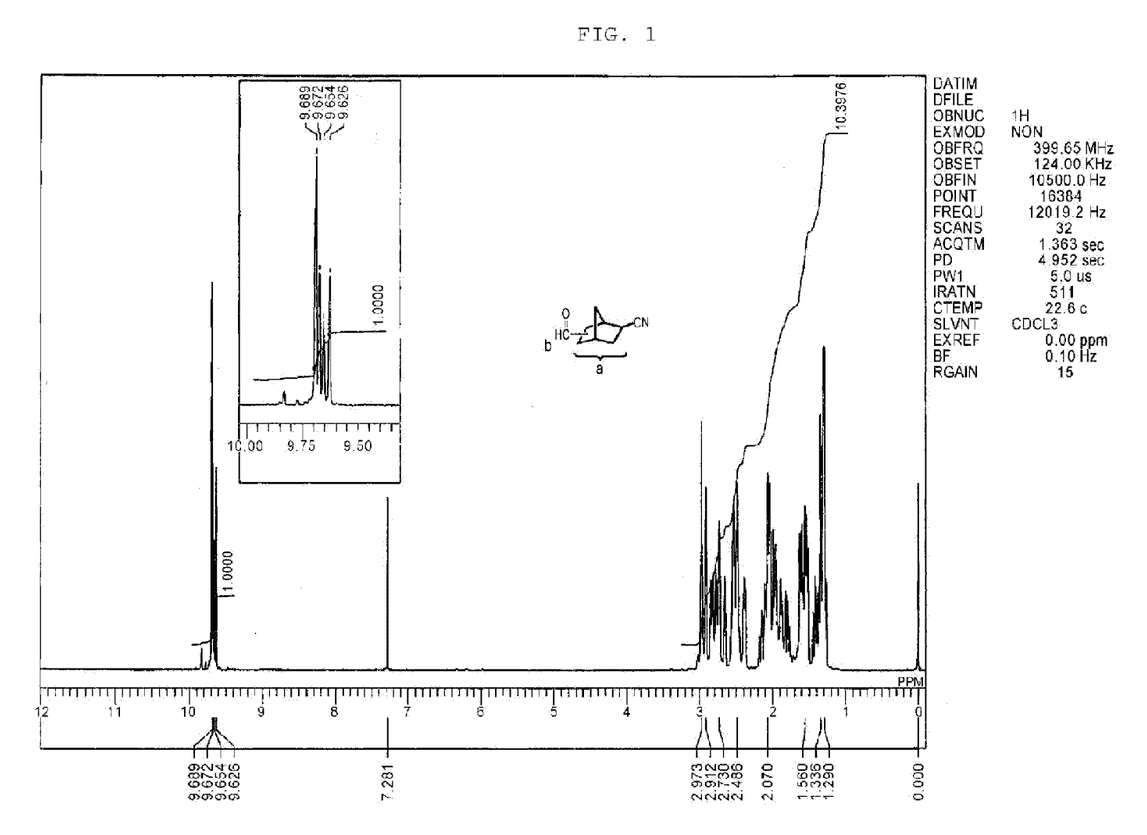
FIG. 1 is a $^1$H-NMR chart of the compound obtained in Example 1.

Then, distillation was performed under a decreased pressure, whereby 264 g of a solution including 250.6 g (1.68 mol) of 2-cyano-5-formyl bicyclo[2.2.1]heptane and 2-cyano-6-formyl bicyclo[2.2.1]heptane was obtained. The solution was purified by distillation under a decreased pressure, whereby 244.7 g (1.64 mol) of a mixture of 2-cyano-5-formyl bicyclo[2.2.1]heptane and 2-cyano-6-formyl bicyclo[2.2.1]heptane was obtained. The $^1$H-NMR chart of the mixture is shown in FIG. 1.

Example 2

Synthesis of 2,5-bisaminomethyl-bicyclo[2.2.1]heptane and 2,6-bisaminomethyl-bicyclo[2.2.1]heptane 89.5 g (0.6 mol) of 2-cyano-5-formyl bicyclo[2.2.1]heptane and 2-cyano-6-formyl bicyclo[2.2.1]heptane obtained in Example 1, 89.5 g of methanol, and 4.5 g (dried mass) of a Raney cobalt catalyst (94% by mass of cobalt, 3.5% by mass of aluminum, and 2.1% by mass of manganese) obtained by developing a cobalt-aluminum alloy containing manganese were put into an electromagnetic stirring type autoclave made of stainless steel having an internal volume of 0.5 Tl, and 24.5 g (1.44 mol) of an ammonia gas was blown thereinto.

Then, after sufficiently replacing with nitrogen, replacement with hydrogen was performed. Furthermore, hydrogen was supplied until the pressure in the autoclave became 1.2 MPaG, and under stirring, the temperature was raised to 100° C., whereby a reaction was started. Since the pressure in the autoclave was decreased with the progress of the reaction, hydrogen was continuously supplied such that the pressure was maintained at 1.2 MPaG, the liquid temperature was adjusted so as to be maintained at 100° C., and a hydrogenation reaction was performed for 6 hours.

After cooling the resultant product to room temperature, the Raney cobalt catalyst was removed by filtration, and ammonia and methanol were distilled off at 4 kPa and 60° C., whereby 102.0 g of a solution including 2,5-bisaminomethyl-bicyclo[2.2.1]heptane and 2,6-bisaminomethyl-bicyclo[2.2.1]heptane was obtained.

102.0 g of the obtained solution including 2,5-bisaminomethyl-bicyclo[2.2.1]heptane and 2,6-bisaminomethyl-bicyclo[2.2.1]heptane was introduced into a 200 mL flask, and distillation was performed under a decreased pressure, whereby 79.0 g of a purified mixture of 2,5-bisaminomethyl-bicyclo[2.2.1]heptane and 2,6-bisaminomethyl-bicyclo[2.2.1]heptane was obtained.

Figure 2:
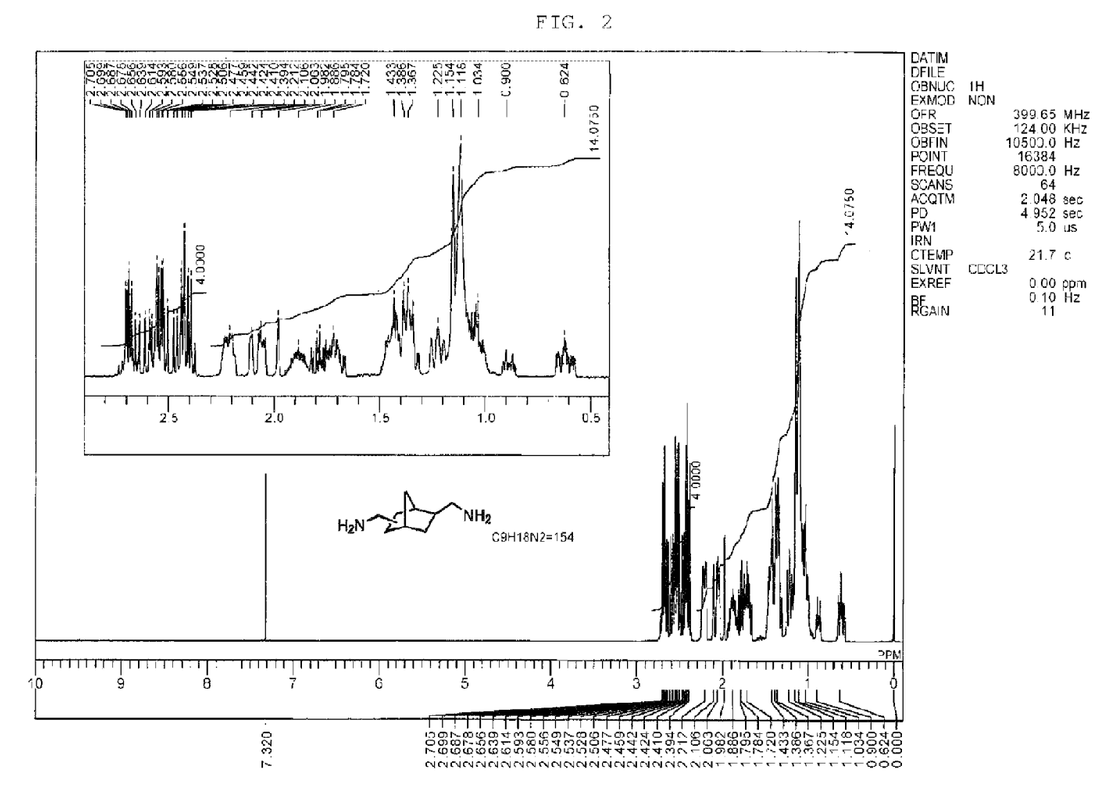
FIG. 2 is a $^1$H-NMR chart of the compound obtained in Example 2.

The $^1$H-NMR chart of the mixture is shown in FIG. 2. The same operation was repeated two times, whereby 158 g of a purified mixture of 2,5-bisaminomethyl-bicyclo[2.2.1]heptane and 2,6-bisaminomethyl-bicyclo[2.2.1]heptane was obtained.

Example 3

Figure 3:
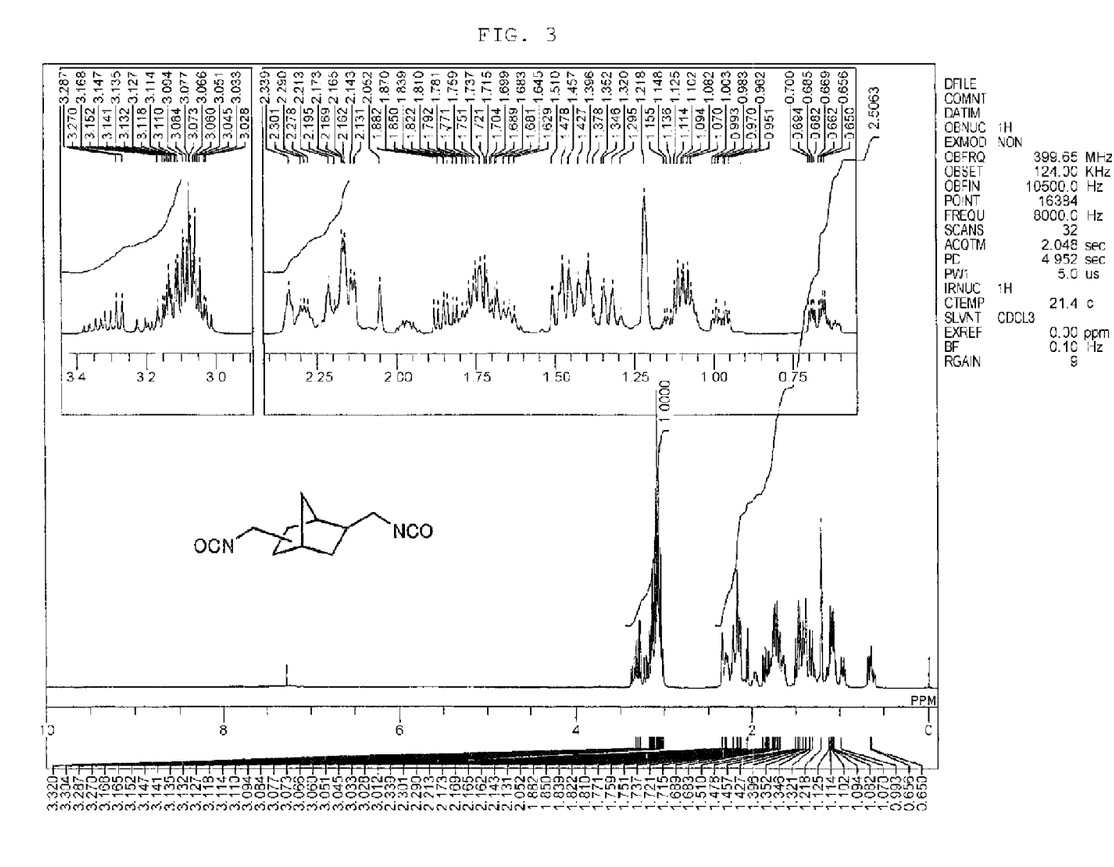
FIG. 3 is a $^1$H-NMR chart of the compound obtained in Example 3.

Synthesis of
2,5-bisisocyanatomethyl-bicyclo[2.2.1]heptane and
2,6-bisisocyanatomethyl-bicyclo[2.2.1]heptane 958 g of orthodichlorobenzene was introduced into a five-neck reaction flask having an internal volume of 2 L equipped with a reflux condenser, a stirring blade, a thermometer, a gas blowing tube, and a raw material introducing tube, and 154.2 g (1.0 mol) of 2,5-bisaminomethyl-bicyclo[2.2.1]heptane and 2,6-bisaminomethyl-bicyclo[2.2.1]heptane obtained in Example 2 and 702 g of orthodichlorobenzene were put into a raw material tank. Then, after raising the temperature of a reaction flask to 120° C. at 0.1 MPa, introductions of hydrochloric acid gas at a rate of 43.8 g/hr from a hydrochloric acid blowing tube and an amine diluted with a solvent at a rate of 428.1 g/hr from the raw material tank through the raw material introducing pump into the reaction flask were started at the same time, and the entire amount was introduced over 2 hours. Furthermore, aging was performed for 1 hour while introducing a hydrochloric acid gas at 20 g/hr. After the reaction was finished, the temperature of a hydrochloride reaction mass was raised to 160° C., then, phosgene was blown in at 100 g/hr (1.0 mol/hr) from a phosgene blowing tube, and the reaction was allowed to proceed for 6 hours while the temperature was maintained. After the reaction was finished, the unreacted phosgene and hydrochloric acid gas in the system were purged with nitrogen, and desolventizing was performed, whereby 200.9 g of a solution including 2,5-bisisocyanatomethyl-bicyclo[2.2.1]heptane and 2,6-bisisocyanatomethyl-bicyclo[2.2.1]heptane was obtained. Furthermore, distillation was performed under a decreased pressure, whereby 175.7 g of a mixture of 2,5-bisisocyanatomethyl-bicyclo[2.2.1]heptane and 2,6-bisisocyanatomethyl-bicyclo[2.2.1]heptane having a purity of 99.0% was obtained. The $^1$H-NMR chart of the mixture is shown in FIG. 3.

Example 4

Synthesis of 2-cyano-5-formyl
bicyclo[2.2.1]heptane and 2-cyano-6-formyl
bicyclo[2.2.1]heptane After a catalyst master liquid was prepared in the same manner as in Example 1, 0.81 mg (0.009 mmol in terms of Rh) of the catalyst master liquid and 218.9 g (1.8 mol) of bicyclo[2.2.1]-5-heptene-2-carbonitrile obtained as a main fraction by distilling the reaction liquid obtained by the method in Reference Example under decreased pressure, and 5.656 g (18.23 mmol) of triphenyl phosphite were introduced into an electromagnetic stirring type autoclave made of SUS316L having an internal volume of 0.5 L, and the mixture was stirred at 25° C., whereby 225.4 g of a Rh catalyst adjusting liquid was obtained. When the amount of acrylonitrile included in the bicyclo[2.2.1]-5-heptene-2-carbonitrile at this time was measured by the above analytical method, the result was 101 ppm (0.417 mmol). The amount corresponds to 46-fold by mole with respect to 1 mole of rhodium used.

Amount of rhodium used: 5 ppmmol with respect to 1 mole of bicyclo[2.2.1]-5-heptene-2-carbonitrile Then, after sufficiently replacing with nitrogen, replacement by a mixed gas having a volume ratio of carbon monoxide/hydrogen of 50/50 was sufficiently performed. The same gas was supplied until the pressure in the autoclave became 0.6 MPaG, and under stirring, the temperature was raised to 80° C., whereby a hydroformylation reaction was started. Since the pressure in the autoclave was decreased with the progress of the reaction, the mixed gas was continuously supplied such that the pressure was maintained at 0.6 MPaG, the liquid temperature was adjusted so as to be maintained at 80° C., and a hydroformylation reaction was performed for 4.9 hours. After the reaction was finished, the mixed gas in the system was purged with nitrogen, whereby 274.8 g of a reaction liquid including 2-cyano-5-formyl bicyclo[2.2.1]heptane and 2-cyano-6-formyl bicyclo[2.2.1]heptane was obtained. When analysis of the reaction liquid was performed, 260.9 g (1.75 mol) of the compounds was found to be contained therein. The reaction yield was 97.2 mol %. The results are shown in Table 1.

Example 5

Synthesis of 2-cyano-5-formyl
bicyclo[2.2.1]heptane and 2-cyano-6-formyl
bicyclo[2.2.1]heptane After a catalyst master liquid was prepared in the same manner as in Example 1, 0.81 mg (0.009 mmol in terms of Rh) of the catalyst master liquid and 218.4 g (1.8 mol) of bicyclo[2.2.1]-5-heptene-2-carbonitrile obtained as a main fraction by distilling the reaction liquid obtained by the method in Reference Example under decreased pressure, and 5.656 g (18.23 mmol) of triphenyl phosphite were introduced into an electromagnetic stirring type autoclave made of SUS316L having an internal volume of 0.5 L, and the mixture was stirred at 25° C., whereby 224.9 g of a Rh catalyst adjusting liquid was obtained. When the amount of acrylonitrile included in the bicyclo[2.2.1]-5-heptene-2-carbonitrile at this time was measured under the above analysis conditions, the result was 201 ppm (0.827 mmol). The amount corresponds to 91-fold by mole with respect to 1 mole of rhodium used.

Amount of rhodium used (condition (1)): 5 ppmmol with respect to 1 mole of bicyclo[2.2.1]-5-heptene-2-carbonitrile A hydroformylation reaction was performed for 5.8 hours under the same reaction conditions as in Example 4. After the reaction was finished, the mixed gas in the system was purged with nitrogen, whereby 274.0 g of a reaction liquid including 2-cyano-5-formyl bicyclo[2.2.1]heptane and 2-cyano-6-formyl bicyclo[2.2.1]heptane was obtained.

When analysis of the reaction liquid was performed, 262.9 g (1.76 mol) of the compounds was found to be contained therein. The reaction yield was 97.8 mol %. The results are shown in Table 1.

Example 6

Synthesis of 2-cyano-5-formyl bicyclo[2.2.1]heptane and 2-cyano-6-formyl bicyclo[2.2.1]heptane After a catalyst master liquid was prepared in the same manner as in Example 1, 0.81 mg (0.009 mmol, in terms of Rh) of the catalyst master liquid and 218.4 g (1.8 mol) of bicyclo[2.2.1]-5-heptene-2-carbonitrile obtained as a main fraction by distilling the reaction liquid obtained by the method in Reference Example under decreased pressure, and 5.656 g (18.23 mmol) of triphenyl phosphite were introduced into an electromagnetic stirring type autoclave made of SUS316L having an internal volume of 0.5 L, and the mixture was stirred at 25° C., whereby 224.9 g of a Rh catalyst adjusting liquid was obtained. When the amount of acrylonitrile included in the bicyclo[2.2.1]-5-heptene-2-carbonitrile at this time was measured under the above analysis conditions, the result was 302 ppm (1.239 mmol). The amount corresponds to 137-fold by mole with respect to 1 mole of rhodium used.

Amount of rhodium used: 5 ppmmol with respect to 1 mole of bicyclo[2.2.1]-5-heptene-2-carbonitrile A hydroformylation reaction was performed for 5.6 hours under the same reaction conditions as in Example 4. After the reaction was finished, the mixed gas in the system was purged with nitrogen, whereby 274.0 g of a reaction liquid including 2-cyano-5-formyl bicyclo[2.2.1]heptane and 2-cyano-6-formyl bicyclo[2.2.1]heptane was obtained. When analysis of the reaction liquid was performed, 261.2 g (1.75 mol) of the compounds was found to be contained therein. The reaction yield was 97.2 mol %. The results are shown in Table 1.

Example 7

Synthesis of 2-cyano-5-formyl bicyclo[2.2.1]heptane and 2-cyano-6-formyl bicyclo[2.2.1]heptane After a catalyst master liquid was prepared in the same manner as in Example 1, 0.81 mg (0.009 mmol in terms of Rh) of the catalyst master liquid and 218.4 g (1.8 mol) of bicyclo[2.2.1]-5-heptene-2-carbonitrile obtained as a main fraction by distilling the reaction liquid obtained by the method in Reference Example under decreased pressure, and 5.656 g (18.23 mmol) of triphenyl phosphite were introduced into an electromagnetic stirring type autoclave made of SUS316L having an internal volume of 0.5 L, and the mixture was stirred at 25° C., whereby 225.0 g of a Rh catalyst adjusting liquid was obtained. When the amount of acrylonitrile included in the bicyclo[2.2.1]-5-heptene-2-carbonitrile at this time was measured under the above analysis conditions, the result was 323 ppm (1.359 mmol). The amount corresponds to 150-fold by mole with respect to 1 mole of rhodium used.

Amount of rhodium used: 5 ppmmol with respect to 1 mole of bicyclo[2.2.1]-5-heptene-2-carbonitrile A hydroformylation reaction was performed for 6.7 hours under the same reaction conditions as in Example 4. After the reaction was finished, the mixed gas in the system was purged with nitrogen, whereby 276.0 g of a reaction liquid including 2-cyano-5-formyl bicyclo[2.2.1]heptane and 2-cyano-6-formyl bicyclo[2.2.1]heptane was obtained. When analysis of the reaction liquid was performed, 258.3 g (1.73 mol) of the compounds was found to be contained therein. The reaction yield was 96.3 mol %. The results are shown in Table 1.

Example 8

Synthesis of 2-cyano-5-formyl bicyclo[2.2.1]heptane and 2-cyano-6-formyl bicyclo[2.2.1]heptane After a catalyst master liquid was prepared in the same manner as in Example 1, 0.81 mg (0.009 mmol in terms of Rh) of the catalyst master liquid and 218.4 g (1.8 mol) of bicyclo[2.2.1]-5-heptene-2-carbonitrile obtained as a main fraction by distilling the reaction liquid obtained by the method in Reference Example under decreased pressure, and 5.656 g (18.23 mmol) of triphenyl phosphite were introduced into an electromagnetic stirring type autoclave made of SUS316L having an internal volume of 0.5 L, and the mixture was stirred at 25° C., whereby 224.8 g of a Rh catalyst adjusting liquid was obtained. When the amount of acrylonitrile included in the bicyclo[2.2.1]-5-heptene-2-carbonitrile at this time was measured under the above analysis conditions, the result was 409 ppm (1.723 mmol). The amount corresponds to 190-fold by mole with respect to 1 mole of rhodium used.

Amount of rhodium used: 5 ppmmol with respect to 1 mole of bicyclo[2.2.1]-5-heptene-2-carbonitrile A hydroformylation reaction was performed for 6.8 hours under the same reaction conditions as in Example 4. After the reaction was finished, the mixed gas in the system was purged with nitrogen, whereby 278.3 g of a reaction liquid including 2-cyano-5-formyl bicyclo[2.2.1]heptane and 2-cyano-6-formyl bicyclo[2.2.1]heptane was obtained. When analysis of the reaction liquid was performed, 259.6 g (1.74 mol) of the compounds was found to be contained therein. The reaction yield was 96.4 mol %. The results are shown in Table 1.

Comparative Example 1

Synthesis of 2-cyano-5-formyl bicyclo[2.2.1]heptane and 2-cyano-6-formyl bicyclo[2.2.1]heptane After a catalyst master liquid was prepared in the same manner as in Example 1, 0.81 mg (0.009 mmol in terms of Rh) of the catalyst master liquid and 219.6 g (1.8 mol) of bicyclo[2.2.1]-5-heptene-2-carbonitrile obtained as a main fraction by distilling the reaction liquid obtained by the method in Reference Example under decreased pressure, and 5.656 g (18.23 mmol) of triphenyl phosphite were introduced into an electromagnetic stirring type autoclave made of SUS316L having an internal volume of 0.5 L, and the mixture was stirred at 25° C., whereby 226.1 g of a Rh catalyst adjusting liquid was obtained. When the amount of acrylonitrile included in the bicyclo[2.2.1]-5-heptene-2-carbonitrile at this time was measured under the above analysis conditions, the result was 460 ppm (1.904 mmol). The amount corresponds to 210-fold by mole with respect to 1 mole of rhodium used.

Amount of rhodium used: 5 ppmmol with respect to 1 mole of bicyclo[2.2.1]-5-heptene-2-carbonitrile A hydroformylation reaction was performed for 5.0 hours under the same reaction conditions as in Example 4. After the reaction was finished, the mixed gas in the system was purged with nitrogen, whereby 258.8 g of a reaction liquid including 2-cyano-5-formyl bicyclo[2.2.1]heptane and 2-cyano-6-formyl bicyclo[2.2.1]heptane was obtained. When analysis of the reaction liquid was performed, 190.6 g (1.28 mol) of the compounds was found to be contained therein. The reaction yield was 71 mol %. The results are shown in Table 1.

TABLE 1

| Example | Amount of AN AN/Rh ratio (mol/mol) | Amount of Rh (ppmmol) | Amount of TPP (mol/mol-Rh) | Reaction time Hr | Yield at reaction time in Table % |
|---|---|---|---|---|---|
| Example 1 | 0.05 | 5 | 2000 | 4.5 | 96.7 |
| Example 4 | 46 | 5 | 2000 | 4.9 | 97.2 |
| Example 5 | 91 | 5 | 2000 | 5.8 | 97.8 |
| Example 6 | 137 | 5 | 2000 | 5.6 | 97.2 |
| Example 7 | 150 | 5 | 2000 | 6.7 | 96.3 |
| Example 8 | 190 | 5 | 2000 | 6.8 | 96.4 |
| Comparative Example 1 | 210 | 5 | 2000 | 5.0 | 71 |

In Examples 1 and 4 to 8, a high yield equal to or greater than 90% could be achieved at a reaction Lime of 4 hours to 7 hours, however, in Comparative Example 1, a yield at a reaction time of 5 hours was 71%.

This application claims priority from Japanese Patent Application No. 2012-247510 filed on Nov. 9, 2012, the content of which is incorporated herein by reference in its entirety.

The invention claimed is:

1. A preparation method of an aldehyde compound, comprising:
    a step of reacting a compound represented by formula (a1) with hydrogen and carbon monoxide in the presence of a metal compound including 5 ppmmol to 10 ppmmol of a metal belonging to Groups 8 to 10 with respect to 1 mole of the compound of a formula (a1) and a phosphorus compound to prepare the aldehyde compound represented by formula (b1)
    wherein the compound of formula (a1) is synthesized from an acrylonitrile,
    wherein the amount of acrylonitrile in the reaction system in the step is equal to or more than 0.05-fold by mole and equal to or less than 200-fold by mole with respect to 1 mole of the metal belonging to Groups 8 to 10, (a1)

wherein n represents 0, 1, or 2, (b1)

2. The preparation method of an aldehyde compound according to claim 1,
    wherein the metal compound including the metal belonging to Groups 8 to 10 is a rhodium compound, a cobalt compound, a ruthenium compound, or an iron compound.

3. The preparation method of an aldehyde compound according to claim 1,
    wherein the metal compound including the metal belonging to Groups 8 to 10 is a rhodium compound.

4. The preparation method of an aldehyde compound according to claim 1,
    wherein the phosphorus compound is a trivalent phosphorus compound.

5. The preparation method of an aldehyde compound according to claim 1,
    wherein the compound represented by formula (a1) is a compound represented by the following chemical formula (1)

(1)

* * * * *